US011282190B2

(12) United States Patent
Niebauer et al.

(10) Patent No.: US 11,282,190 B2
(45) Date of Patent: Mar. 22, 2022

(54) SYSTEMS AND METHODS FOR HAIR COVERAGE ANALYSIS

(71) Applicant: The Procter & Gamble Company, Cincinnati, OH (US)

(72) Inventors: Michael Frederick Niebauer, Cincinnati, OH (US); Faiz Feisal Sherman, Mason, OH (US); Raghunandan Melkote Kainkaryam, Cincinnati, OH (US); Ankur Purwar, Singapore (SG); Stephen Casperson, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 127 days.

(21) Appl. No.: 16/413,920

(22) Filed: May 16, 2019

(65) Prior Publication Data

US 2019/0355115 A1 Nov. 21, 2019

Related U.S. Application Data

(60) Provisional application No. 62/672,791, filed on May 17, 2018.

(51) Int. Cl.
*G06K 9/62* (2006.01)
*G06T 7/00* (2017.01)
(Continued)

(52) U.S. Cl.
CPC .............. *G06T 7/0012* (2013.01); *G06N 3/08* (2013.01); *G06N 20/00* (2019.01);
(Continued)

(58) Field of Classification Search
CPC ........ G06N 20/00–20; G06N 3/08–088; G06T 2207/20081; G06T 2207/20084;
(Continued)

(56) References Cited

U.S. PATENT DOCUMENTS 2,946,725 A 7/1960 Norris
3,070,510 A 12/1962 Cooley
(Continued)

FOREIGN PATENT DOCUMENTS

CN 104586362 A 5/2015
CN 105441213 A 3/2016
(Continued)

OTHER PUBLICATIONS

Ramos et al., "Female Pattern Hair Loss: a clinical and pathophysiological review", ABD: Anais Brasileiros De Dermatologia, Official publication of the Brazilian Society of Dermatology, Jul.-Aug. 2015, pp. 1-29. (Year: 2015).*

(Continued)

*Primary Examiner* — Brian Werner
(74) *Attorney, Agent, or Firm* — Linda M. Sivik

(57) ABSTRACT

Disclosed are hair analysis systems and methods comprising: (a) a step to capture an image at least of the top of the head of a user at an image capture unit and to send the image from the image capture unit to a hair analysis unit; (b) a step to analyze the user's hair coverage and/or scalp coverage condition at hair analysis unit, based on the image from the image capture unit by using a deep neural network that predicts user's hair coverage and/or scalp coverage relative to a gender population and is trained on class labels acquired by crowd sourcing, and to provide an analysis result to a display unit; and (c) a step to display at a display unit the analysis result to the user. The present invention provides the system and the method with an improved sensitivity.

11 Claims, 2 Drawing Sheets

(51) Int. Cl.
*G06N 20/00* (2019.01)
*G06N 3/08* (2006.01)
*A45D 44/00* (2006.01)

(52) U.S. Cl.
CPC .................. *A45D 2044/007* (2013.01); *G06T 2207/20081* (2013.01); *G06T 2207/20084* (2013.01)

(58) Field of Classification Search
CPC .. G06T 7/0012–0016; A45D 2044/007; A45D 44/005; H04N 2005/2726; A61B 5/448
See application file for complete search history.

(56) References Cited

U.S. PATENT DOCUMENTS

| | | |
|---|---|---|
| 3,429,963 A | 2/1969 | Shedlovsky |
| 3,506,720 A | 4/1970 | Model et al. |
| 3,535,421 A | 10/1970 | Briner |
| 3,538,230 A | 11/1970 | Pader |
| 3,678,154 A | 7/1972 | Widder |
| 3,689,637 A | 9/1972 | Pader |
| 3,696,191 A | 10/1972 | Weeks |
| 3,711,604 A | 1/1973 | Colodney et al. |
| 3,737,533 A | 6/1973 | Moon et al. |
| 3,862,307 A | 1/1975 | Di |
| 3,911,104 A | 10/1975 | Harrison |
| 3,935,306 A | 1/1976 | Roberts et al. |
| 3,959,458 A | 5/1976 | Agricola |
| 3,988,443 A | 10/1976 | Ploger et al. |
| 3,991,177 A | 11/1976 | Vidra et al. |
| 4,040,858 A | 8/1977 | Wason |
| 4,051,234 A | 9/1977 | Gieske |
| 4,058,595 A | 11/1977 | Colodney |
| 4,138,477 A | 2/1979 | Gaffar |
| 4,154,815 A | 5/1979 | Pader |
| 4,183,914 A | 1/1980 | Gaffar |
| 4,304,766 A | 12/1981 | Chang |
| 4,355,022 A | 10/1982 | Rabussay |
| 4,590,066 A | 5/1986 | Parran, Jr. et al. |
| 4,627,977 A | 12/1986 | Gaffar |
| 4,661,341 A | 4/1987 | Benedict et al. |
| 4,846,650 A | 7/1989 | Benedict et al. |
| 4,877,603 A | 10/1989 | Degenhardt |
| 4,980,153 A | 12/1990 | Jackson et al. |
| 4,992,420 A | 2/1991 | Neeser |
| 5,000,939 A | 3/1991 | Dring et al. |
| 5,037,637 A | 8/1991 | Gaffar et al. |
| 5,626,838 A | 5/1997 | Cavanaugh, Jr. |
| 5,827,505 A | 10/1998 | Hughes et al. |
| 5,939,052 A | 8/1999 | White, Jr. et al. |
| 6,251,372 B1 | 6/2001 | Witt et al. |
| 6,707,929 B2 | 3/2004 | Marapane |
| 7,079,158 B2 | 7/2006 | Lambertsen |
| 7,104,800 B2 | 9/2006 | Ortiz-valero |
| 7,435,794 B2 | 10/2008 | Lukyanov et al. |
| 7,437,344 B2 | 10/2008 | Peyrelevade |
| 8,119,162 B2 | 2/2012 | Miksa |
| 8,168,600 B2 | 5/2012 | Dokka |
| 8,241,651 B2 | 8/2012 | Lahann |
| 8,338,115 B2 | 12/2012 | Adler |
| 8,360,973 B2 | 1/2013 | Bazin |
| 8,484,155 B2 | 7/2013 | Yamaguchi |
| 8,871,920 B2 | 10/2014 | Purschke |
| 9,457,071 B2 | 10/2016 | Hide |
| 9,518,265 B2 | 12/2016 | Hohlig |
| 9,709,576 B2 | 7/2017 | Hide |
| 9,732,348 B2 | 8/2017 | Cauchard |
| 9,902,961 B2 | 2/2018 | Dausse |
| 9,976,145 B2 | 5/2018 | Jarosch |
| 9,996,674 B2 | 6/2018 | Segman |
| 10,001,496 B2 | 6/2018 | Jung |
| 10,231,531 B2 | 3/2019 | Witchell |
| 10,650,289 B2 * | 5/2020 | Szegedy ............ G06N 3/0454 |
| 10,676,396 B2 | 6/2020 | Johannsmann et al. |
| 10,994,919 B2 | 5/2021 | Hochberg et al. |
| 2002/0065452 A1 | 5/2002 | Bazin |
| 2002/0150287 A1 | 10/2002 | Kobayashi |
| 2002/0183988 A1 | 12/2002 | Skaanning |
| 2003/0014324 A1 | 1/2003 | Donovan |
| 2004/0236592 A1 | 11/2004 | Aleles |
| 2006/0085274 A1 | 4/2006 | Sottery |
| 2006/0149151 A1 | 7/2006 | Ladjevardi |
| 2006/0178904 A1 | 8/2006 | Aghassian |
| 2007/0054261 A1 | 3/2007 | Sherman |
| 2007/0058858 A1 | 3/2007 | Harville |
| 2008/0097814 A1 | 4/2008 | Koustoumbardi |
| 2008/0152600 A1 | 6/2008 | Huang et al. |
| 2010/0106679 A1 | 4/2010 | Yamaguchi |
| 2010/0254581 A1 | 10/2010 | Neeser |
| 2011/0016001 A1 | 1/2011 | Schieffelin |
| 2012/0041282 A1 | 2/2012 | Nichol |
| 2012/0190627 A1 | 7/2012 | Delattre |
| 2012/0320191 A1 | 12/2012 | Meschkat |
| 2013/0323242 A1 | 12/2013 | Everett |
| 2013/0332451 A1 | 12/2013 | Camplejohn et al. |
| 2014/0028822 A1 | 1/2014 | Khadavi |
| 2014/0081035 A1 | 3/2014 | Krishnan |
| 2014/0216492 A1 | 8/2014 | Magri |
| 2014/0378810 A1 | 12/2014 | Davis |
| 2015/0045631 A1 | 2/2015 | Ademola |
| 2015/0217465 A1 | 8/2015 | Krenik |
| 2015/0329863 A1 | 11/2015 | Cauchard et al. |
| 2015/0353933 A1 | 12/2015 | Miyakawa et al. |
| 2016/0061602 A1 | 3/2016 | Fessi |
| 2016/0326530 A1 | 11/2016 | Dausse et al. |
| 2017/0004558 A1 * | 1/2017 | Abramowitz ...... G06Q 30/0631 |
| 2017/0107515 A1 | 4/2017 | Eberly et al. |
| 2017/0270593 A1 | 9/2017 | Sherman |
| 2018/0040052 A1 | 2/2018 | Robinson |
| 2018/0040053 A1 | 2/2018 | Robinson |
| 2018/0116583 A1 | 5/2018 | Cook |
| 2018/0140248 A1 | 5/2018 | Chandra |
| 2018/0223285 A1 | 8/2018 | Hohlig |
| 2018/0225673 A1 | 8/2018 | Dubey |
| 2018/0235535 A1 | 8/2018 | Cook |
| 2018/0247365 A1 | 8/2018 | Cook |
| 2018/0253866 A1 * | 9/2018 | Jain ........................ G06N 7/005 |
| 2018/0349979 A1 | 12/2018 | Robinson |
| 2019/0035149 A1 | 1/2019 | Chen |
| 2019/0048348 A1 | 2/2019 | Velasquez |
| 2019/0048349 A1 | 2/2019 | Velasquez et al. |
| 2019/0112593 A1 | 4/2019 | Penner |
| 2019/0183232 A1 | 6/2019 | Knuebel et al. |
| 2019/0209077 A1 * | 7/2019 | Charraud ............... A61B 5/448 |
| 2019/0350514 A1 | 11/2019 | Purwar |
| 2019/0355119 A1 | 11/2019 | Hu |
| 2020/0000697 A1 | 1/2020 | Velasquez et al. |
| 2020/0002703 A1 | 1/2020 | Velasquez |
| 2020/0055659 A1 | 2/2020 | Hochberg |
| 2020/0330353 A1 | 10/2020 | Velasquez et al. |
| 2021/0059754 A1 | 3/2021 | Kasprzak |
| 2021/0106696 A1 | 4/2021 | Dalma-weiszhausz et al. |

FOREIGN PATENT DOCUMENTS

| | | |
|---|---|---|
| DE | 102017214250 A1 | 2/2019 |
| FR | 3020465 A1 | 10/2015 |
| GB | 490384 A | 8/1938 |
| JP | 2004354207 A | 12/2004 |
| JP | 3163309 U | 9/2010 |
| JP | 2017009426 A | 1/2017 |
| JP | 2018041434 A | 3/2018 |
| JP | 2019212073 A | 12/2019 |
| JP | 2020171428 A | 10/2020 |
| KR | 101456942 B1 | 11/2014 |
| KR | 102047237 B1 | 12/2019 |
| RU | 2306921 C1 | 9/2007 |
| TW | I670047 B | 9/2019 |
| WO | 9960167 A1 | 11/1999 |
| WO | 0187245 A2 | 11/2001 |
| WO | 0191602 A2 | 12/2001 |
| WO | 02083737 A1 | 10/2002 |
| WO | 2006055902 A2 | 5/2006 |

(56) References Cited

FOREIGN PATENT DOCUMENTS

| WO | 2010006215 A1 | 1/2010 |
|---|---|---|
| WO | 2011085727 A1 | 7/2011 |
| WO | 2015140722 A1 | 9/2015 |
| WO | 2016176203 A1 | 11/2016 |
| WO | 2017139417 A1 | 8/2017 |
| WO | 2017207455 A1 | 12/2017 |
| WO | 2018173073 A1 | 9/2018 |
| WO | 2018202065 A1 | 11/2018 |
| WO | 2019177451 A1 | 9/2019 |

OTHER PUBLICATIONS

Geron, "Introducing capsule networks", O'Reilly, https://www.oreilly.com/content/introducing-capsule-networks/, Feb. 6, 2018, pp. 1-7. (Year: 2018).*
All Office Actions; U.S. Appl. No. 16/441,749.
International Search Report and Written Opinion; Application No. PCT/US2019/032404; dated Jul. 30, 2019; 11 pages.
Schwartz, J.R. et al., "The role of oxidative damage in poor scalp health: ramifications to causality and associated hair growth", International Journal of Cosmetic Science, vol. 37, No. Suppl. 2, Sp. Iss. SI, Dec. 2015, pp. 9-15.
U.S. Unpublished U.S. Appl. No. 16/953,385, filed Nov. 20, 2020, to Supriya Punyani et al.
Unpublished U.S. Appl. No. 16/587,224, filed Sep. 30, 2019, to Robert Joseph Senior, et al.
"Jack Florek '17 presents at ACS in San Francisco", Emmanuel College, retrieved from http://gerdonlab.blogs.emmanuel.edu/2017/04/04/jack-florek-17-presents-acs-san-francisco/, Oct. 15, 2018, 6 pages.
All Office Actions, U.S. Appl. No. 16/587,224.
All Office Actions, U.S. Appl. No. 16/953,385.
Bawazer et al., "Efficient Selection of Biomineralizing DNA Aptamers Using Deep Sequencing and Population Clustering", ACS Nano, vol. 8, No. 1, 2014, pp. 1-10.
Database WPI, XP002785798, Week 201649, 2017, Thomson Scientific, London GB, AN 2016-20069A.
Eifler, Electronic Nose-Based Fusarium Detection and Deoxynivalenol Aptamer Development, Dissertation, Jul. 2014, 106 pages.
Fujii et al., "Pesticide vapor sensing using an aptamer, nanopore, and agarose gel on a chip", Lab on a Chip, vol. 17, No. 14, 2017, pp. 2421-2425.
Gao et al., "Post-Selex optimization of aptamers", Analytical and Bioanalytical Chemistry, Springer, vol. 408, No. 17, 2016, pp. 4567-4573.
Hasegawa et al., "Methods for Improving Aptamer Binding Affinity", Molecules, vol. 21, No. 4, 2016, pp. 1-15.
Hurot et al., "Bio-Inspired Strategies for Improving the Selectivity and Sensitivity of Artificial Noses: A Review", Sensors, vol. 20, No. 6, 2020, pp. 1-28.
Janas et al., "The selection of aptamers specific for membrane molecular targets", Cellular & Molecular Biology Letters, vol. 16, No. 1, 2011, pp. 25-39.
John et al., "ANYL 154: DNA aptamers that bind with high affinity to hydroxyapatite", ACS National Meeting & Exposition; 253rd National Meeting of The American-Chemical-Society (ACS) on Advanced Materials, Technologies, Systems, and Processes, American Chemical So, vol. 253, Apr. 2017, p. ANYL154.
Komarova et al., "Selection, Characterization, and Application of ssDNA Aptamer against Furaneol", Molecules, vol. 23, No. 12, 2018, pp. 1-15.
Kuznetsov et al., "Aptamer based vanillin sensor using an ion-sensitive field-effect transistor", Microchimica Acta, vol. 185, No. 1, 2017, 26 pages.
Li et al., "VEGF induces proliferation of human hair follicle dermal papilla cells through VEGFR-2-mediated activation of ERK", Experimental Cell Research, vol. 318, No. 14, 2012, pp. 1633-1640.
Low et al., "DNA aptamers bind specifically and selectively to (1-3)-beta-d-glucans", Biochemical and Biophysical Research Communications, vol. 378, No. 4, 2009, pp. 701-705.
Nonaka et al., "Screening and improvement of an anti-VEGF DNA aptamer", Molecules, vol. 15, No. 1, 2010, pp. 215-225.
Pillaiyar et al., "Downregulation of melanogenesis: drug discovery and therapeutic options", Drug Discovery Today, vol. 22, No. 2, Feb. 2017, pp. 282-298.
Shibata et al., "The cell wall galactomannan antigen from Malassezia furfur and Maiassezia pachydermatis contains-1,6-linked linear galactofuranosyl residues and its detection has diagnostic potential", Microbiology, vol. 155, No. 10, 2009, pp. 3420-3429.
Tang et al., "Improved detection of deeply invasive candidiasis with DNA aptamers specific binding to (1-3)-[beta]-D-glucans from Candida albicans", European Journal of Clinical Microbiology & Infectious diseases, vol. 35, No. 4, 2016, pp. 587-595.
Velegraki et al., "Malassezia Infections in Humans and Animals: Pathophysiology, Detection and Treatment", PLOS Pathogens, vol. 11, No. 1, Jan. 2015, pp. 1-6.
"How C-Lab is Preparing for a Future Full of Potential—Part 1: C-Lab Inside", Samsung Newsroom, 5 pgs, Jan. 2, 2020.
All Office Actions; U.S. Appl. No. 17/230,121.
All Office Actions; U.S. Appl. No. 17/326,505.
All Office Actions; U.S. Appl. No. 17/386,580.
Aram Huvis Co., Ltd, Aram HUVIS' skin & Hair Analysis System, APM (Aramo Professional Microscope), Jun. 15, 2017, 1 pg.
Artificial Intelligence in Skin and Hair Diagnostic Technology, year 2020, 1 pg.
Benhabiles et al., "Deep learning based detection of hair loss levels from facial images", year 2019, 6 pgs.
Chang et al., "A mobile device-based hairy scalp diagnosis system using deep learning techniques", IEEE 2nd Global Conference on Life Sciences and Technologies, year 2020, pp. 145-146.
H. Shih, "A precise automatic system for the hair assessment in hair-care diagnosis applications", Skin Research and Technology, 2015, pp. 500-507.
Huang et al., "A cloud-based intelligent skin and scalp analysis system", Dec. 2018, 5 pages.
Illuminate, powerpoint presentation, property of Aduivo Diagnostics PVT LTD, 10 pgs.
Infusing Technology to advance the growth of the Hair Care Industry, HairAnalysis-KritiKal, Year 2021, 4 pgs.
Lee et al., "An intelligent hair and scalp analysis system using camera sensors and Norwood-Hamilton model", International Journal of Innovative Computing, Information and Control, vol. 14, No. 2, pp. 503-518, Apr. 2018.
Su et al., "An Intelligent Scalp Inspection and Diagnosis System for Caring Hairy Scalp Health", pp. 508-509, 2018.
U.S. Unpublished U.S. Appl. No. 17/230,121, filed Apr. 14, 2021, to first inventor Supriya Punyani et al.
U.S. Unpublished U.S. Appl. No. 17/326,505, filed May 21, 2021, to first inventor Supriya Punyani et al.
U.S. Unpublished U.S. Appl. No. 17/386,580, filed Jul. 28, 2021, to Ankur Purwar et al.
Wan-Jung Chang et al., "Scalp Eye: A Deep Learning Based Scalp Hair Inspection and Diagnosis System for Scalp Health", IEEE Access, Jul. 21, 2020, vol. 8, Digital Object Identifier 10.1109/Access.2020.3010847, pp. 134826-134837.
Wang et al., "Development and experimental evaluation of machine-learning techniques for an intelligent hairy scalp detection system", Applied Sciences, Year 2018, 28 pgs.
"Connected scalp advisor shows root of the problem" URL Link: https://www.youtube.com/watch?v=Y-oAEiCO1-g, Jan. 9, 2019.

* cited by examiner

SYSTEMS AND METHODS FOR HAIR COVERAGE ANALYSIS

FIELD OF THE INVENTION

The present application relates generally to hair coverage analysis systems and methods to capture an image of at least the top of the head of a user, analyze the user's hair coverage and/or scalp coverage condition by using a deep neural network that is trained on class labels acquired by crowd sourcing; and predicts user's hair coverage and/or scalp coverage relative to a gender population, and to provide the analysis result to the user. The present invention provides the system and the method with an improved sensitivity.

BACKGROUND OF THE INVENTION

Across the globe, premature hair loss and thinning is one of the largest unmet consumer needs that impacts over half of the population. The majority of those concerned about the status of their hair amount do not take immediate action because they are unaware of the true extent of their condition. While there are diagnostic techniques available they have been regulated to clinics and doctor's offices providing a more analog analysis. If an individual had better access to assess their condition early on, they may be able to choose to do a better job at maintaining their current hair amount. Recent improvements in digital imaging technology, in particular images or selfies of consumers, have increased the ability to leverage image analysis techniques and therefore improve the accessibility and speed of 'in hand' consumer diagnostics. However, with the wide variety of consumers characteristics and 'selfie' conditions have made it difficult to accurately access the condition and recommend a treatment protocol without the need of a more manual consultation. Further, these methods, systems and assessments rely on predetermined information about the hair physical properties and appearance and thus fails to generalize for real life hair conditions. Thus, there still remains a need to provide an improved method of conveniently determining the amount of hair a person currently has, which can then be used to help provide a customized hair loss prevention product or regimen recommendation.

Assessing hair condition is of interest in order to understand, for example, the degree of hair coverage and/or scalp coverage. Such assessment is also of interest in order to demonstrate the efficacy of treatments used for preventing and/or treating hair loss.

Accordingly, the present invention has met this need for a system and method of evaluating consumer hair loss with improved sensitivity to assess real life hair conditions, and providing such evaluation results; a customized product recommendation based on the evaluation result; and a customized hair style recommendation based on the evaluation result.

SUMMARY OF THE INVENTION

A hair analysis system comprising:
a) an image capture unit to capture an image of at least the top of the head of a user and to send the image to a hair analysis unit;
b) a hair analysis unit: to analyze the user's hair coverage and/or scalp coverage based on the image by using a deep neural network that predicts user's hair coverage and/or scalp coverage relative to a gender population; and to provide an analysis result to a display unit wherein the analysis result is at least one of the followings:
  the analyzed hair coverage and/or scalp coverage condition;
  hair prediction based on the analyzed hair coverage and/or scalp coverage condition;
  hair product recommendation based on the analyzed hair coverage and/or scalp coverage condition;
  hair product usage recommendation based on the analyzed hair coverage and/or scalp coverage condition; and
  hair style recommendation based on the analyzed hair coverage and/or scalp coverage conditions.
c) a display unit to display the analysis result to the user.

A hair analysis method comprising:
a) a step to capture an image of at least the top of the head of a user at an image capture unit and to send the image from the image capture unit to a hair analysis unit;
b) a step to analyze the user's hair coverage and/or scalp coverage at hair analysis unit, based on the image from the image capture unit by using a deep neural network that predicts user's hair coverage and/or scalp coverage relative to a gender population; and to provide an analysis result to a display unit wherein the analysis result is at least one of the followings:
  the analyzed hair coverage and/or scalp coverage condition;
  hair prediction based on the analyzed hair coverage and/or scalp coverage condition;
  hair product recommendation based on the analyzed hair coverage and/or scalp coverage condition;
  hair product usage recommendation based on the analyzed hair coverage and/or scalp coverage condition; and
  hair style recommendation based on the analyzed hair coverage and/or scalp coverage condition;
c) a step to display at a display unit the analysis result to the user.

The system and method of analyzing user's hair coverage and/or scalp coverage conditions provides improved sensitivity to assess real life hair conditions, and providing such analysis results. By the use of a deep neural network (DNN) in the method and the system, to provide an user with hair analysis of how the user looks from an image in which the user's hair coverage and/or scalp coverage on top of head are shown. This DNN based system uses very little image pre-processing that reduces the dependence on pre-determined information about the image and helps to generalize, thus, evaluating consumer hair and/or scalp conditions with improved sensitivity to assess real life hair and/or scalp conditions.

BRIEF DESCRIPTION OF THE DRAWINGS

It is to be understood that both the foregoing general description and the following detailed description describe various non-limiting examples and are intended to provide an overview or framework for understanding the nature and character of the claimed subject matter. The accompanying drawings are included to provide a further understanding of various non-limiting examples, and are incorporated into and constitute a part of this specification. The drawings illustrate various non-limiting examples described herein, and together with the description serve to explain the principles and operations of the claimed subject matter.

DETAILED DESCRIPTION OF THE INVENTION

Figure 1:
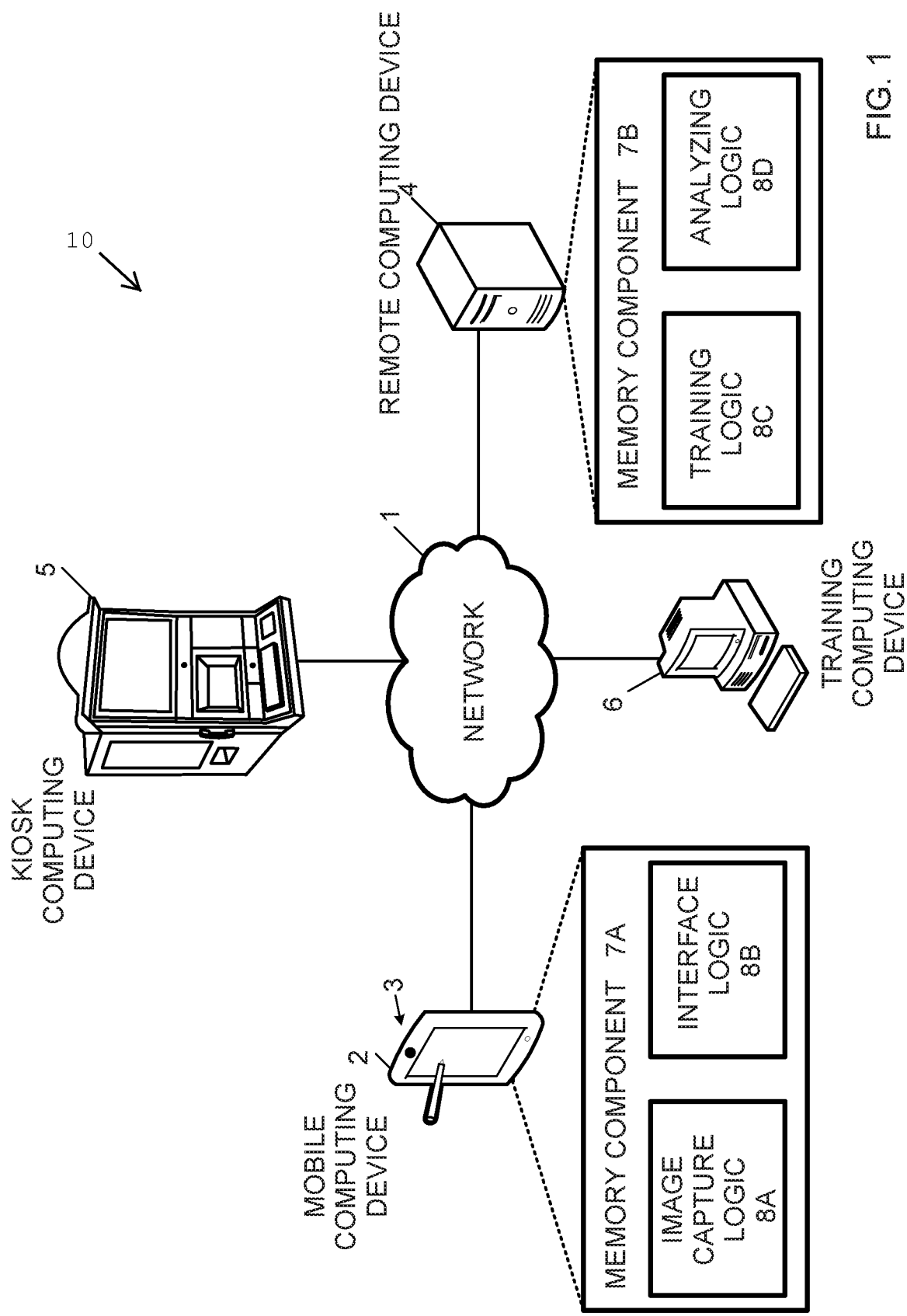
FIG. 1 is a non-limiting example depicting a system for capturing an image of a user, analyzing the image, and providing a customized product recommendation, according to the present invention described herein

"Deep neural network" is a type of feed-forward artificial neural network with multiple layers of neurons or units that build a hierarchy of learned features or concepts representing the input. Examples of these DNN could be Convolutional Neural Networks (CNN) or Deep Capsule Networks (DCN).

"Coupled," when referring to various components of the system herein, means that the components are in electrical, electronic, and/or mechanical communication with one another.

"Data augmentation" means altering data associated with a training image or other image to create additional samples for the image.

"Feature vector" means a series of features that contain information describing one or more characteristics of an object in a digital image. Each feature in the feature vector is typically represented by one or more numbers, but any suitable indicator may be used, as desired (letters, symbols, colors, etc.)

"Image capture device" means a device such as a digital camera capable of capturing an image of a user; further could be a "Video Capture Device" such as a digital camera capable of capturing a video of a user; further could be a 3-D Image Capture Device.

"Macro features" are relatively large bodily features found on or at top of head or near the face of a human. Macro features include, without limitation, top of head, face shape, ears, eyes, mouth, nose, hair, and eyebrows.

"Micro features" are features such as scalp area, hair amount, hair thickness amount, hair coverage, scalp coverage, hair partition. Micro features do not include macro features.

"Model" herein refers to a mathematical equation, algorithm, or computer software used to predict, describe, or imitate a set of circumstances, a system, or a naturally occurring phenomenon.

"Selfie" refers to a digital image, digital video, still image or 3-D scan of a person taken by that person, taken by another person, or an automated image capture system (e.g., photo booth or security camera). Further, the selfie may include a digital image, digital video, still image or 3-D scan of the top of the head of a person, "User" herein refers to a person who uses at least the features provided herein, including, for example, a device user, a product user, a system user, and the like.

Building the Model

The inputs used to train the diagnostic model may be images, videos, 3D scans, etc. of at least the top-of-the-head from hundreds of individuals (covering variations in gender, ethnicity, hair color, location, backdrop, etc.). These inputs may be graded for hair-coverage by a panel of expert graders or a crowd of novice graders, also known as crowd sourcing. One approach may be to arrange the inputs into groups based on hair-coverage patterns (e.g. low, medium, high, etc.). Another approach may be to use a pairwise comparison method where a pair of inputs is shown to a grader and they are asked to choose the one with higher (or lower) hair-coverage. A collection of these pairwise choices from single or multiple graders may be aggregated into a hair-coverage score or rank for individuals whose inputs are graded. The hair-coverage scale or scores or ranks may be further binned into a few hair-coverage levels (e.g., 0 to 3) or used as a continuous hair-coverage value (e.g., 0 to 1). The inputs along with their corresponding hair-coverage group labels or levels or scores may then be used to train a deep neural network model to predict the hair-coverage label, level, or score given an input. Separate hair-coverage prediction models may be trained for individuals with different attributes such as gender, ethnicities, etc. A pre-step of the diagnostic process may include asking the individual to specify these attributes (such as gender, ethnicity, etc.) or use a separate deep neural network model to predict these attributes from the input so as to direct the input to the corresponding attribute-specific hair-coverage model.

Another pre-step of the diagnostic may include the identification of input quality issues (e.g., input is too blurry, too dark, too bright, does not have top-of-the-head clearly included, etc.) and providing correction feedback to generate improved inputs. The input quality identification may also be predicted via a deep neural network model trained on inputs with the corresponding input quality issue labels.

Neural Network

In the present invention, for a neural network, takes an input (e.g. an image) and produces an output (e.g. a prediction about the image like classifying its content). This consists of several (hence "deep") "hidden" (or intermediate) layers that successively transform the input data (e.g. pixel values) to produce an output value (e.g. probability of image classification). The weights or parameters of the hidden layers are "learned" (e.g. gradient descent by back-propagation) by showing the network input-output pairs (hence labeled data is needed—e.g. images with class labels). The idea of using depth (multiple hidden layers) is to create a hierarchy of learned features/layers that would build on each other to produce a complex understanding of the input (e.g. from raw pixels in image→identifying lines/edges/colors→object parts (circle/square)→small objects (wheel/window)→larger objects/scene (car)).

Convolutional Neural Network (CNN)

In the present invention, for a convolutional neural network (CNN) the hidden layers use a specific operation called a "convolution" to only process data for a "receptive field" (for example, a convolutional kernel could "look" at a 3×3 pixel window in the input image at a time and apply a transformation locally and repeat this process same across the whole image grid). Typically, a CNN can include several successive convolution, pooling, activation layers (for feature extraction) leading up to fully-connected layers that produces the desired output (for prediction).

Capsule Network (CapsNet)

In the present invention, CNNs may not directly use the relative relationship of learned features (e.g. eyes are above nose and mouth) to do classification. Capsule network (CapsNets) try to explicitly learn the pose (translation and rotation) of object parts in composing a complex object. CapsNets can therefore potentially use much fewer labeled examples to achieve the same classification performance of CNNs.

Image Capture Unit

The image capture unit is used to capture an image of a user and to send the image to a hair analysis unit.

The image of the user herein is an image showing user's top of head, or a 3-D video of a whole head, or user's hair and face. In the image, it may be a ratio of the face size to the image size ratio is around 20% to 70%, so that the image shows more than 70% of the outline of the hair, or more than 80%, or more than 90%, or more than 95% of the outline of the hair. The image herein can be anything such as selfie and video. The image may further undergo a quality check or pre-processing to insure a full hair view of acceptable quality is present. The image may have an automatic guidance to capture an optimal head selfie. A non-limiting example would be such guidance could be an automatic number such a measured distance from a camera or a certain angle or via an audio command. Another non-limiting example would be guidance to adjust for lighting conditions. Further, for hair coverage on a scalp, the image may further look at different zones on the scalp, for example, which area on the scalp may have less or more hair coverage, and accessing a certain zone for measures which may lead to a product recommendation.

The image capture unit can be connected to the hair analysis unit by wired or wireless connection.

Q&A User Interface Unit

This unit, which is optionally included into the system and/or method of the present invention, is to provide a question for the user at the user interface; to receive an answer from the user; and to send the answer to a hair analysis unit.

This unit can provide a list of questions for the consumer at the user interface, wherein each question having a defined set of answers; to send the answer chosen by the consumer at the user interface to the hair analysis unit.

Questions herein are, for example, those relating to use's hair coverage and/or scalp coverage conditions, those relating to user's habit associated with hair; those relating to user's product preference, those relating to user's hair style preference, those relating to user's geographic information, those relating to user's gender, those relating to user's age; those relating to user's life style.

The answer can be utilized for providing hair analysis result at the hair coverage and/or scalp coverage analysis unit. The answer can be sent to the hair analysis unit in any form, for example, can be sent as it is, or can be sent as a score calculated from the answer.

The Q&A interface unit can be connected with the hair coverage and/or scalp coverage analysis unit by wired or wireless connection. The Q&A interface unit can be connected with the image capture unit by wired or wireless connection, or can be independent from the image capture unit, or can be physically located together with the image capture unit, for example, within the same mobile computing device.

Hair Analysis Unit

The hair analysis unit is to analyze the user's hair coverage and/or scalp coverage condition based on the image of at least the top of the head of a user by using a deep neural network; and to provide an analysis result to a display unit wherein the analysis result is at least one of the followings: the analyzed hair coverage and/or scalp coverage condition; hair prediction based on the analyzed hair coverage and/or scalp coverage condition; hair product recommendation based on the analyzed hair coverage and/or scalp coverage condition; hair product usage recommendation based on the analyzed hair coverage and/or scalp coverage condition; and hair style recommendation based on the analyzed hair coverage and/or scalp coverage condition.

The hair analysis unit additionally may preprocess the image, wherein preprocessing comprises: determining an anchor feature on the image and altering the image to place the anchor feature in a predetermined position.

The hair condition analysis may be made in the hair analysis unit by the steps comprising:

Preprocessing;

Applying a deep neural network (DNN) to extract micro and micro features including both face and hair features; and Providing analyzed hair coverage and/or scalp coverage conditions.

Hair conditions to be analyzed herein are at least one of the followings: hair and/or scalp coverage, scalp area, hair amount, hair thickness amount, hair partition and combinations thereof.

For the analysis of these hair coverage and/or scalp coverage conditions, the present invention can provide improved sensitivity by incorporation of the capture of an image of at least the top of the head of a user.

Hair prediction, hair product recommendation, hair product usage recommendation, and hair style recommendation are all based on such analyzed hair coverage and/or scalp coverage condition.

The hair analysis unit can be connected with the display unit by wired or wireless connection.

Display Unit

The display unit is to display the analysis result to the user, wherein the analysis result is at least one of the followings: the analyzed hair coverage and/or scalp coverage condition which may include hair and/or scalp coverage, scalp area, hair amount, hair thickness amount, hair partition and combinations thereof; hair prediction based on the analyzed hair coverage and/or scalp coverage condition; hair product recommendation based on the analyzed hair coverage and/or scalp coverage condition; hair product usage recommendation based on the analyzed hair coverage and/or scalp coverage condition; and hair style recommendation based on the analyzed hair coverage and/or scalp coverage condition.

The display showing the hair product recommendation and/or hair product usage recommendation, also shows an option for the user to purchase the product.

The analysis result can be shown, for example, by numerical data such as absolute values, relative values, indexes, and/or colors with or without indications. Alternatively, or concurrently, the analyzed hair coverage and/or scalp coverage condition can be shown, for example, by cartoon, and/or by indication and/or highlight on the image to show the area for improvement.

The display unit can be physically located together with the image capture unit and/or the Q&A user interface unit, for example, within the same mobile computing device. Alternatively, the display unit can be located separately from any of them.

EXAMPLES

The systems and methods herein may use a trained a deep neural network such as a CNN or DCN, to analyze hair conditions of a user by analyzing a captured image of the user. The CNN comprises multiple layers of neuron collections that use the same filters for each pixel in a layer. Using the same filters for each pixel in the various combinations of partially and fully connected layers reduces memory and processing requirements of the system.

In some instances, the system may include a preprocessing stage followed by a stage for CNN or DCN training and image analysis. During preprocessing, one or more hair features common to most users, such as scalp area, hair amount, hair thickness amount, hair coverage, scalp coverage, hair partition, ("anchor features"), in a received image may be detected. The system may detect the anchor feature(s) using known edge detection techniques, shape detection techniques, and the like. Based on the location of the anchor feature(s), the image may be scaled and rotated to make the image substantially level and with the anchor feature(s) arranged in a predetermined position in the final image. In this way, training images can be consistently aligned, thus providing more consistent training and analysis. The image may then be cropped to a predetermined area of pixels as input for further processing.

Preprocessing may also include image normalization. For example, global contrast normalization may be utilized to standardize the training images (and/or images of users) to address the variability that could be introduced by real life selfie capture condition.

In some instances, data augmentation may be performed to create additional samples from an inputted image. The additional samples are used to train the CNN or DCN to tolerate variation in input images. This helps improve the accuracy of the model. In other words, the CNN or DCN is able to extract the information & relationships of important features necessary for a suitable analysis in spite of differences in, for example, the way people take photographs, the conditions in which photos are taken, and the hardware used to take a photo. The additional samples generated by data augmentation can also force the CNN or DCN to learn to rely on a variety of features for hair condition analysis rather than one particular feature, and may prevent over-training of the CNN or DCN. Some non-limiting examples of data augmentation include randomly enlarging or shrinking the image, randomly rotating the image in a clockwise or counter-clockwise direction, randomly cropping the image, and/or randomly changing the saturation and/or exposure of the image. In some instances the image data may be augmented by subjecting the input image to random vertical dropout, in which a random column of pixels is removed from the image.

The CNN or DCN herein may be trained using a deep learning technique, which allows the CNN or DCN to learn what portions of an image contribute to skin, face features, hair characteristics, etc., much in the same way as a mammalian visual cortex learns to recognize important features in an image. In some instances, the CNN training may involve using mini-batch stochastic gradient descent (SGD) with Nesterov momentum (and/or other algorithms). An example of utilizing a stochastic gradient descent is disclosed in U.S. Pat. No. 8,582,807.

DCN is composed of many capsules. A capsule is a small group of neurons that learns to detect a particular object (e.g., a rectangle) within a given region of the image, and it outputs a vector (e.g., an 8-dimensional vector) whose length represents the estimated probability that the object is present, and whose orientation (e.g., in 8D space) encodes the object's pose parameters (e.g., precise position, rotation, etc.). Much like a regular neural network, a DCN is organized in multiple layers. The capsules in the lowest layer are called primary capsules: each of them receives a small region of the image as input (called its receptive field), and it tries to detect the presence and pose of a particular pattern, for example a rectangle. Capsules in higher layers, called routing capsules, detect larger and more complex objects, such as boats. The primary capsule layer may be implemented using a few regular convolutional layers. For example, two convolutional layers could be used that output 256 6×6 features maps containing scalars. These feature maps could be reshaped to get 32 6×6 maps containing 8-dimensional vectors. Finally, a squashing function may be applied to ensure these vectors have a length between 0 and 1 (to represent a probability).

The capsules in the next layers may also try to detect objects and their pose using an algorithm called routing by agreement. The routing-by-agreement algorithm may involve a few iterations of agreement-detection+routing-update (this may happen for each prediction, not just once, and not just at training time).

Source: www.oreilly.com/ideas/introducing-capsule-networks

In some instances, the DNN may be trained by providing an untrained DNN with a multitude of captured images to learn from. In some instances, the DNN can learn to identify portions of an image that contribute to a particular hair coverage and/or scalp coverage condition through a process called supervised learning. "Supervised learning" generally means that the DNN is trained by analyzing images in which the hair coverage and/or scalp coverage of the person in the image is predetermined. Depending on the accuracy desired, the number of training images may vary from a few images to a multitude of images (e.g., hundreds or even thousands) to a continuous input of images (i.e., to provide continuous training).

The systems and methods herein utilize a trained DNN that is capable of accurately analyzing hair condition of a user for a wide range of hair types and styles. To provide analyzed hair condition, an image of a user is forward-propagating through the trained DNN. The DNN analyzes the image and identifies portions of the image that contribute to the hair condition such as hair coverage and/or scalp coverage. The DNN then uses the identified portions to analyze hair condition of the user.

In some instances, the DNN analysis, analyzed hair coverage and/or scalp condition and/or target condition, optionally in conjunction with habits and practices input provided by a user, can be used to help provide a hair prediction, hair care product recommendation, hair product usage recommendation and/or hair style recommendation.

FIG. 1 depicts a system 10 for capturing an image of a user, analyzing the image, and providing a customized product recommendation. The system 10 may include a network 1, which may be embodied as a wide area network (such as a mobile telephone network, a public switched telephone network, a satellite network, the internet, etc.), a local area network (such as wireless-fidelity, Wi-Max, ZigBee™, Bluetooth™, etc.), and/or other forms of networking capabilities. Coupled to the network 1 are a mobile computing device 2, a remote computing device 4, a kiosk computing device 5, and a training computing device 6.

The mobile computing device 2 may be a mobile telephone, a tablet, a laptop, a personal digital assistant and/or other computing device configured for capturing, storing, and/or transferring an image such as a digital photograph. Accordingly, the mobile computing device 2 may include an image capture device 3 such as a digital camera and/or may be configured to receive images from other devices. The mobile computing device 2 may include a memory component 7A, which stores image capture logic 8A and interface logic 8B. The memory component 7A may include random access memory (such as SRAM, DRAM, etc.), read only memory (ROM), registers, and/or other forms of computing storage hardware. The image capture logic 8A and the interface logic 8B may include software components, hardware circuitry, firmware, and/or other computing infrastructure, as described herein. As described in more detail below, the image capture logic 8A may facilitate capturing, storing, preprocessing, analyzing, transferring, and/or performing other functions on a digital image of a user. The interface logic 8B may be configured for providing one or more user interfaces to the user, which may include questions, options, and the like. The mobile computing device 2 may also be configured for communicating with other computing devices via the network 1.

The remote computing device 4 may also be coupled to the network 1 and may be configured as a server (or plurality of servers), personal computer, mobile computer, and/or other computing device configured for creating and training a convolutional neural network capable of analyze hair conditions of a user by identifying portions of a captured image that contribute to a particular hair condition. The remote computing device 4 may include a memory component 7B, which stores training logic 8C and analyzing logic 8D. The training logic 8C may facilitate creation and/or training of the DNN, and thus may facilitate creation of and/or operation of the DNN. For example, the DNN may be stored as logic 8C, 8D in the memory component 7B of a remote computing device 4. The analyzing logic 8D may cause the remote computing device 4 to receive data from the mobile computing device 2 (or other computing device) and process the received data for providing analyzed hair coverage and/or scalp coverage, product recommendation, hair style recommendation, etc.

The system 10 may also include a kiosk computing device 5, as illustrated in FIG. 1. The kiosk computing device 5 may operate similar to the mobile computing device 2, but may also be able to dispense one or more products and/or receive payment in the form of cash or electronic transactions. In some instances, the kiosk computing device 5 may also be configured to facilitate training of the DNN, as described in more detail below with regard to the training computing device 6.

A training computing device 6 may be coupled to the network 1 to facilitate training of the DNN. For example, a trainer may provide one or more digital images of a face or skin or hair to the DNN via the training computing device 6. The trainer may also provide information and other instructions to inform the DNN which assessments are correct and which assessments are not correct. Based on the input from the trainer, the DNN may automatically adapt, as described in more detail below.

It should be understood that while the kiosk computing device 5 is depicted as a vending machine type of device, this is a non-limiting example. Further non-limiting examples may utilize a mobile device that also provides payment and/or production dispensing. Similarly, the kiosk computing device 5, the mobile computing device 2, and/or the training computing device 6 may be utilized for training the DNN. As a consequence, the hardware and software depicted for the mobile computing device 2 and the remote computing device 4 may be included in the kiosk computing device 5, the training computing device 6, and/or other devices. Similarly, a hardware and software may be included in one or more of the mobile computing device 2, the remote computing device 4, the kiosk computing device 5, and the training computing device 6.

It should also be understood that while the remote computing device 4 is depicted in FIG. 1 as performing the deep neural network processing, this is merely an example. The deep neural network processing may be performed by any suitable computing device, as desired.

Figure 2:
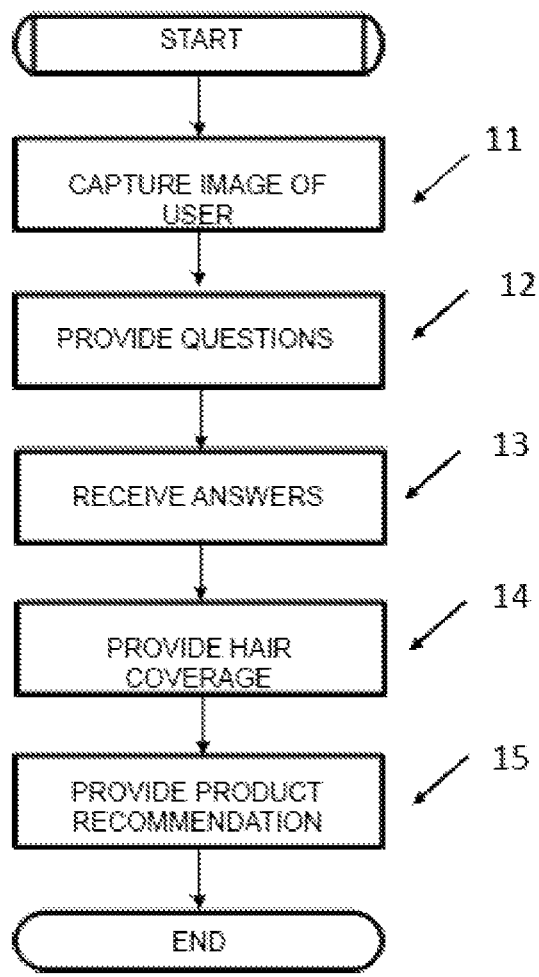
FIG. 2 is a non-limiting example depicting a flowchart for providing customized product recommendations, according to the present invention described herein.

FIG. 2 depicts a flowchart for providing customized product recommendations, and is described herein. In block 11, an image of a user may be captured. In block 12, questions may be provided to the user. In block 13, answers to the questions may be received from the user. In block 14, analyzed hair coverage and/or scalp coverage condition may be provided to the user. In block 15, a customized product recommendation may be provided to the user.

Additional Examples/Combinations

A. A hair analysis system comprising:
  a. an image capture unit to capture an image at least of the top of the head of a user and to send the image to a hair analysis unit;
  b. a hair analysis unit: to analyze the user's hair coverage and/or scalp coverage based on the image by using a deep neural network that predicts user's hair coverage and/or scalp coverage relative to a gender population; and to provide an analysis result to a display unit wherein the analysis result is at least one of the followings:
    the analyzed hair coverage and/or scalp coverage condition;
    hair prediction based on the analyzed hair coverage and/or scalp coverage condition;
    hair product recommendation based on the analyzed hair coverage and/or scalp coverage condition;
    hair product usage recommendation based on the analyzed hair coverage and/or scalp coverage condition; and
    hair style recommendation based on the analyzed hair coverage and/or scalp coverage conditions;
  c. a display unit to display the analysis result to the user.

B. The system according to Paragraph A, wherein the deep neural network is trained on class labels acquired by crowd sourcing.

C. The system according to Paragraph A-B, wherein the system further comprises a Q&A user interface unit to provide a question for the user at the user interface; to receive an answer from the user; and to send the answer to the analysis unit.

D. The system according to Paragraph A-C, wherein the answer is utilized for providing the analysis result.

E. The system according to Paragraph A-D, wherein the system using a Convolutional Neural Network.

F. The system according to Paragraph A-E, wherein the system using a Deep Capsule Network.

G. The system according to Paragraph A-F, wherein the display showing the hair product recommendation and/or hair product usage recommendation, also shows an option for the user to purchase the product.

H. The system according to Paragraph A-G, wherein the hair coverage and/or scalp coverage to be analyzed is at least one of the followings: hair and/or scalp coverage, scalp area, hair amount, hair thickness amount, hair partition and combinations thereof.

I. A hair analysis method according to Paragraph A-H, comprising:
  a) a step to capture an image of at least the top of the head of a user at an image capture unit and to send the image from the image capture unit to a hair analysis unit;
  b) a step to analyze the user's hair coverage and/or scalp coverage at hair analysis unit, based on the image from the image capture unit by using a deep neural network that: 1) is trained on class labels acquired by crowd sourcing; and 2) predicts user's hair coverage and/or scalp coverage relative to a gender population; and to provide an analysis result to a display unit wherein the analysis result is at least one of the followings:
    the analyzed hair coverage and/or scalp coverage condition;

hair prediction based on the analyzed hair coverage and/or scalp coverage condition;

hair product recommendation based on the analyzed hair coverage and/or scalp coverage condition;

hair product usage recommendation based on the analyzed hair coverage and/or scalp coverage condition; and hair style recommendation based on the analyzed hair coverage and/or scalp coverage condition;

c) a step to display at a display unit the analysis result to the user

J. The method according to Paragraph A-I, the deep neural network is trained on class labels acquired by crowd sourcing.

K. The method according to Paragraph A-J, wherein the method further comprises a step at Q&A user interface unit to provide a question for the user; to receive an answer from the user; and to send the answer to the analysis unit.

L. The method according to Paragraph A-K, wherein the answer is utilized for providing the analysis result.

M. The method according to Paragraph A-L, wherein the display unit showing the hair product recommendation and/or hair product usage recommendation, also shows an option for the user to purchase the product.

N. The method according to Paragraph A-M, wherein the hair coverage and/or scalp coverage to be analyzed is at least one of the followings: hair and/or scalp coverage, scalp area, hair amount, hair thickness amount, hair partition and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair analysis system comprising:
   a) an image capture device used to capture an image at least of the top of the head of a user wherein the image capture unit sends the image to a hair analysis unit by wired or wireless connection to the hair analysis unit;
   a hair analysis unit: to analyze the user's hair coverage and/or scalp coverage based on the image by using a deep neural network that predicts user's hair coverage and/or scalp coverage relative to a gender population wherein the deep neural network is a Deep Capsule Network;
   and to provide an analysis result to a display unit wherein the analysis result is at least one of the followings:
   the analyzed hair coverage and/or scalp coverage condition;
   hair prediction based on the analyzed hair coverage and/or scalp coverage condition;
   hair product recommendation based on the analyzed hair coverage and/or scalp coverage condition;
   hair product usage recommendation based on the analyzed hair coverage and/or scalp coverage condition; and
   hair style recommendation based on the analyzed hair coverage and/or scalp coverage conditions;
   b) a display unit to display the analysis result to the user; wherein the deep neural network is trained on class labels acquired by crowd sourcing.

2. The system of claim 1, wherein the system further comprises a Q&A user interface unit to provide a question for the user at the user interface; to receive an answer from the user; and to send the answer to the analysis unit.

3. The system of claim 2, wherein the answer is utilized for providing the analysis result.

4. The system of claim 1, wherein the system using a Convolutional Neural Network.

5. The system of claim 1, wherein the display showing the hair product recommendation and/or hair product usage recommendation, also shows an option for the user to purchase the product.

6. The system of claim 1, wherein the hair coverage and/or scalp coverage to be analyzed is at least one of the followings: hair and/or scalp coverage, scalp area, hair amount, hair thickness amount, hair partition and combinations thereof.

7. A hair analysis method comprising:
   a) a step to capture an image of at least the top of the head of a user at an image capture device used to capture an image at least of the top of the head of a user wherein the image capture device sends the image to a hair analysis unit by wired or wireless connection to the hair analysis unit;
   b) a step to analyze the user's hair coverage and/or scalp coverage at hair analysis unit, based on the image from the image capture device by using a deep neural network that predicts user's hair coverage and/or scalp coverage relative to a gender population wherein the deep neural network is a Deep Capsule Network;
   and to provide an analysis result to a display unit wherein the analysis result is at least one of the followings:
   the analyzed hair coverage and/or scalp coverage condition;
   hair prediction based on the analyzed hair coverage and/or scalp coverage condition;
   hair product recommendation based on the analyzed hair coverage and/or scalp coverage condition;
   hair product usage recommendation based on the analyzed hair coverage and/or scalp coverage condition; and
   hair style recommendation based on the analyzed hair coverage and/or scalp coverage condition;
   c) a step to display at a display unit the analysis result to the user; wherein the deep neural network is trained on class labels acquired by crowd sourcing.

8. The method of claim 7, wherein the method further comprises a step at Q&A user interface unit to provide a question for the user; to receive an answer from the user; and to send the answer to the analysis unit.

9. The method of claim 8, wherein the answer is utilized for providing the analysis result.

10. The method of claim 7, wherein the display unit showing the hair product recommendation and/or hair product usage recommendation, also shows an option for the user to purchase the product.

11. The method of claim 7, wherein the hair coverage and/or scalp coverage to be analyzed is at least one of the followings: hair and/or scalp coverage, scalp area, hair amount, hair thickness amount, hair partition and combinations thereof.

* * * * *